(12) United States Patent
Shiozaki et al.

(10) Patent No.: US 11,839,749 B2
(45) Date of Patent: Dec. 12, 2023

(54) SYRINGE CAP, SYRINGE WITH NEEDLE, AND PREFILLED SYRINGE FORMULATION

(71) Applicants: Taisei Kako Co., Ltd., Osaka (JP); Chugai Seiyaku Kabushiki Kaisha, Tokyo (JP)

(72) Inventors: Rieko Shiozaki, Tokyo (JP); Yuji Yamanaka, Tokyo (JP); Taiji Horita, Osaka (JP); Ippei Matsumoto, Osaka (JP); Kensuke Taniguchi, Osaka (JP)

(73) Assignees: Taisei Kako Co., Ltd., Osaka (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/315,460

(22) PCT Filed: Jun. 4, 2015

(86) PCT No.: PCT/JP2015/066209
§ 371 (c)(1),
(2) Date: Dec. 1, 2016

(87) PCT Pub. No.: WO2015/186792
PCT Pub. Date: Dec. 10, 2015

(65) Prior Publication Data
US 2017/0197039 A1    Jul. 13, 2017

(30) Foreign Application Priority Data

Jun. 4, 2014    (JP) ................................ 2014-115936

(51) Int. Cl.
*A61M 5/32*    (2006.01)
(52) U.S. Cl.
CPC ........ *A61M 5/3202* (2013.01); *A61M 5/3213* (2013.01)

(58) Field of Classification Search
CPC ................ A61M 5/3202; A61M 5/321; A61M 2005/3212; A61M 2005/3215;
(Continued)

(56) References Cited

U.S. PATENT DOCUMENTS

| 3,342,319 A | * | 9/1967 | Faulseit | ................ | A61M 5/002 |
| | | | | | 206/365 |
| 4,740,204 A | | 4/1988 | Masters et al. | | |

(Continued)

FOREIGN PATENT DOCUMENTS

| CN | 101072595 A | 11/2007 |
| CN | 101252959 A | 8/2008 |

(Continued)

OTHER PUBLICATIONS

International Preliminary Report and Written Opinion dated Dec. 15, 2016 in connection with PCT/JP2015/066209.

(Continued)

*Primary Examiner* — Amber R Stiles
*Assistant Examiner* — Hong-Van N Trinh
(74) *Attorney, Agent, or Firm* — Brooks Kushman P.C.

(57) ABSTRACT

Provided is a syringe cap including a projection extending in the circumferential direction of a cap body, wherein the projection includes an apex located radially outward of the cap body from the outer circumferential surface of the cap body, a first inclined surface having a starting end located at the apex and having a terminal end located at a position on the side closer to the proximal end of the cap body than the starting end is, and a second inclined surface having a starting end located at the apex and on the outer circumferential surface of the cap body having a terminal end located at a position on the side closer to the distal end of the cap body than the starting end is, on the outer circumferential surface of the cap body, and the shortest distance from the (Continued)

starting end to the terminal end of the first inclined surface is smaller than the shortest distance from the starting end to the terminal end of the second inclined surface.

12 Claims, 19 Drawing Sheets

(58) Field of Classification Search
CPC .............. A61M 5/3212; A61M 5/3213; A61M 5/3245; A61M 2005/3109; A61M 5/3216; A61M 5/1626; A61M 5/3243; A61M 2005/312; A61M 25/0612; Y10S 128/919; A61B 5/150259; A61B 5/150374; A61B 5/150534; A61B 5/150541; A61B 5/150549; A61B 5/150557; A61B 5/150564; A61B 5/150572; A61B 5/15058; A61B 5/150587; A61B 5/150595; A61B 5/150603; A61B 5/15061; A61B 5/150618; A61B 5/150625; A61B 5/150694; A61B 5/150717; A61B 5/150351

See application file for complete search history.

(56) References Cited

U.S. PATENT DOCUMENTS

| | | | |
|---|---|---|---|
| 4,929,232 A | | 5/1990 | Sweeney et al. |
| 4,990,141 A * | | 2/1991 | Byrne ..................... A61M 5/24 604/198 |
| 5,308,330 A | | 5/1994 | Grimard |
| 5,417,326 A * | | 5/1995 | Winer ................... A61M 5/002 206/365 |
| 5,540,666 A | | 7/1996 | Barta et al. |
| 5,582,594 A * | | 12/1996 | Chen .................... A61M 5/3202 604/110 |
| 5,752,936 A | | 5/1998 | Chen |
| 6,551,286 B1 * | | 4/2003 | Claessens ........... A61M 5/3202 128/919 |
| 6,719,732 B2 | | 4/2004 | Courteix |
| 7,297,136 B2 | | 11/2007 | Wyrick |
| 7,621,891 B2 | | 11/2009 | Wyrick |
| 7,635,356 B2 | | 12/2009 | Stamp |
| 7,645,265 B2 * | | 1/2010 | Stamp .................. A61M 5/2033 604/134 |
| 7,878,245 B2 | | 2/2011 | Maxon et al. |
| 7,905,352 B2 | | 3/2011 | Wyrick |
| 7,927,303 B2 | | 4/2011 | Wyrick |
| 7,931,618 B2 | | 4/2011 | Wyrick |
| D651,308 S | | 12/2011 | Crawford et al. |
| 8,105,271 B2 | | 1/2012 | Matusch |
| 8,187,224 B2 | | 5/2012 | Wyrick |
| 8,323,251 B2 * | | 12/2012 | West ..................... A61B 5/1405 206/365 |
| 8,870,828 B2 * | | 10/2014 | West ..................... A61B 5/1405 206/365 |
| 8,888,713 B2 | | 11/2014 | Robert et al. |
| 8,998,855 B2 | | 4/2015 | Hudson et al. |
| 9,089,655 B2 | | 7/2015 | Tsals |
| 9,095,288 B2 | | 8/2015 | Robert et al. |
| D748,778 S * | | 2/2016 | Shiozaki ...................... D24/130 |
| 9,271,668 B2 | | 3/2016 | Robert et al. |
| 9,615,783 B2 | | 4/2017 | Robert et al. |
| 9,649,441 B2 | | 5/2017 | Barrow-Williams |
| 9,687,184 B2 | | 6/2017 | Robert et al. |
| 10,085,680 B2 | | 10/2018 | Robert et al. |
| 10,166,334 B2 | | 1/2019 | Wyrick |
| 10,349,880 B2 | | 7/2019 | Robert et al. |
| 2003/0060760 A1 | | 3/2003 | Botich |
| 2005/0165360 A1 * | | 7/2005 | Stamp .................. A61M 5/2033 604/187 |
| 2006/0129122 A1 * | | 6/2006 | Wyrick ............... A61M 5/2033 604/506 |
| 2006/0173408 A1 | | 8/2006 | Wyrick |
| 2006/0178634 A1 | | 8/2006 | Wyrick |
| 2007/0017532 A1 | | 1/2007 | Wyrick |
| 2007/0017533 A1 | | 1/2007 | Wyrick |
| 2008/0039789 A1 | | 2/2008 | Wyrick |
| 2008/0132838 A1 | | 6/2008 | Wyrick |
| 2008/0154199 A1 | | 6/2008 | Wyrick |
| 2008/0228143 A1 * | | 9/2008 | Stamp .................. A61M 5/2033 604/157 |
| 2008/0319346 A1 | | 12/2008 | Crawford |
| 2009/0095475 A1 | | 4/2009 | Ravi |
| 2009/0187153 A1 * | | 7/2009 | West ................. A61B 5/150587 604/263 |
| 2009/0198196 A1 * | | 8/2009 | West .................... A61B 5/1405 604/263 |
| 2009/0204026 A1 | | 8/2009 | Crawford et al. |
| 2010/0069846 A1 * | | 3/2010 | Stamp .................. A61M 5/2033 604/135 |
| 2010/0094217 A1 | | 4/2010 | Wyrick |
| 2010/0100039 A1 | | 4/2010 | Wyrick |
| 2011/0077324 A1 | | 3/2011 | Ravi et al. |
| 2011/0166474 A1 | | 7/2011 | Crawford |
| 2011/0166475 A1 | | 7/2011 | Crawford |
| 2011/0166476 A1 | | 7/2011 | Crawford |
| 2011/0226646 A1 | | 9/2011 | Wyrick |
| 2012/0065593 A1 | | 3/2012 | Donald |
| 2013/0096462 A1 * | | 4/2013 | West .................... A61B 5/1405 600/576 |
| 2014/0358037 A1 | | 12/2014 | Crawford |
| 2016/0135725 A1 | | 5/2016 | Crawford |
| 2017/0251966 A1 | | 9/2017 | Crawford et al. |
| 2018/0280621 A1 | | 10/2018 | Wyrick |
| 2019/0000366 A1 | | 1/2019 | Crawford et al. |

FOREIGN PATENT DOCUMENTS

| | | |
|---|---|---|
| CN | 102245232 A | 11/2011 |
| CN | 102264419 A | 11/2011 |
| CN | 102266230 A | 12/2011 |
| CN | 202620380 U | 12/2012 |
| JP | 44-12316 B1 | 6/1969 |
| JP | 2-5968 A | 1/1990 |
| JP | 8-206203 A | 8/1996 |
| JP | 2000-79163 A | 3/2000 |
| JP | 2007-518507 A | 7/2007 |
| JP | 2007-209508 A | 8/2007 |
| JP | 2008-522659 A | 7/2008 |
| JP | 2009-090140 A | 4/2009 |
| JP | 2010-207369 A | 9/2010 |
| WO | WO93/017732 A | 9/1993 |
| WO | WO94/022511 A | 10/1994 |

OTHER PUBLICATIONS

European Search Report dated Jan. 29, 2018 connection with European Appl. No. 15803488.4.
Chinese Office Action dated Mar. 4, 2019 in connection with related Chinese Appl. No. 201580029428.1.
Korean Office Action dated Oct. 12, 2021 in connection with related Korean Appl. No. 2016-7035804.
Korean Office Action dated Mar. 28, 2023 in connection with related Korean Appl. No. 2016-7035804.

* cited by examiner

SYRINGE CAP, SYRINGE WITH NEEDLE, AND PREFILLED SYRINGE FORMULATION

CROSS-REFERENCE TO RELATED APPLICATION

This application claims priority to Japanese Patent Application No. 2014-115936, the disclosure of which is incorporated herein by reference in its entirety.

FIELD

The present invention relates to a syringe cap configured to protect a needle, a syringe with a needle, and a prefilled syringe formulation.

BACKGROUND

Conventionally, a prefilled syringe including a cylindrical syringe body internally filled with drug, a needle attached to the distal end of the syringe body, and a plunger that is inserted into the syringe body and is slidable in the axial direction of the syringe body is known.

Generally, the prefilled syringe of this type further includes a syringe cap that is detachably attached to the syringe body so as to cover the needle, thereby preventing a user's hand, finger, or the like from being accidentally pricked by the needle before use.

Such a syringe cap generally has a cylindrical cap body into which the needle is inserted from the proximal end toward the distal end and which is detachably attached to the syringe body to which the needle is attached (see Patent Literature 1, for example).

In such a syringe cap, since the cap body occupies a large region in the entire syringe cap, the cap body of the syringe cap is generally pinched when using the prefilled syringe, and the cap body is detached by being pulled in a direction away from the syringe body.

CITATION LIST

Patent Literature

Patent Literature 1: JP 2000-079163 A

SUMMARY

Technical Problem

By the way, such a syringe cap is generally a resin molded product, and therefore the outer circumferential surface of the cap body is smooth and slippery. Therefore, when the syringe cap is detached from the syringe body, it may be difficult to detach the syringe cap because the tension applied to the cap body is not transmitted to the entire syringe cap.

Therefore, the present invention provides a syringe cap that suppresses slip in detachment from a syringe body, and a syringe with a needle and a prefilled syringe formulation that include the syringe cap.

Solution to Problem

A syringe cap according to the present invention includes: a cylindrical cap body into which a needle is inserted from the proximal end toward the distal end and which is detachably attached to a syringe body to which the needle is attached; and at least one projection projecting from the outer circumferential surface of the cap body and extending in the circumferential direction of the cap body, wherein the projection includes: an apex located radially outward of the cap body from the outer circumferential surface of the cap body; a first inclined surface having a starting end located at the apex and having a terminal end located at a position on the side closer to the proximal end of the cap body than the starting end is, on the outer circumferential surface of the cap body; and a second inclined surface having a starting end located at the apex and having a terminal end located at a position on the side closer to the distal end of the cap body than the starting end is, on the outer circumferential surface of the cap body, and the shortest distance from the starting end to the terminal end of the first inclined surface is smaller than the shortest distance from the starting end to the terminal end of the second inclined surface.

According to one aspect of the present invention, the configuration can be such that the cap body includes a tapered portion having an outer diameter that continuously decreases from the proximal end side toward the distal end side, and the projection is arranged in the tapered portion.

In this case, the configuration can be such that the inclination angle of the first inclined surface with respect to the axis of the cap body is the same as the inclination angle of the second inclined surface with respect to the axis of the cap body.

According to another aspect of the present invention, it is preferable that the projection be provided along the entire circumference of the cap body.

According to another aspect of the present invention, it is preferable that the projection comprises a plurality of projections. It is preferable that the number of projections be 4 or more. The upper limit of the number of projections differs depending on the cap size and is not specifically limited, but is, for example, 20 or less, preferably 15 or less. In particular, for a syringe cap with a volume of 1 mL, the number of projections is preferably 3 to 15, further preferably 3 to 12.

In this case, it is preferable that the plurality of projections be arranged at least in the central region in a direction in which the axis of the cap body extends, on the outer circumferential surface of the cap body.

In this case, it is preferable that at least one of the plurality of projections be higher than the other projections.

In this case, the configuration can be such that all of the plurality of projections arranged in the central region have the same height.

In this case, the configuration can be such that the plurality of projections include a projection that is arranged in at least one of a region on the distal end side from the central region and a region on the proximal end side from the central region, on the outer circumferential surface of the cap body, and that is higher than the projections arranged in the central region.

In this case, it is preferable that the plurality of projections include projections that are arranged respectively in the region on the distal end side and the region on the proximal end side and that are higher than the plurality of projections arranged in the central region.

In this case, it is preferable that the projection arranged in the region on the distal end side be higher than the projection arranged in the region on the proximal end side.

In this case, it is preferable that the projection arranged in the region on the distal end side be highest in the plurality of projections.

A syringe with a needle according to the present invention includes: a syringe body that is internally fillable with drug;

a needle attached to the distal end of the syringe body; and a syringe cap detachably attached to the syringe body and configured to cover the needle, wherein the syringe cap is the syringe cap according to any one of the aforementioned aspects.

A prefilled syringe formulation of the present invention includes: a syringe body internally filled with drug; a needle attached to the distal end of the syringe body; and a syringe cap detachably attached to the syringe body and configured to cover the needle, wherein the syringe cap is the syringe cap according to any one of the aforementioned aspects.

In this case, it is preferable that the aforementioned prefilled syringe formulation be a self-injectable formulation.

DESCRIPTION OF EMBODIMENTS

Figure 1:
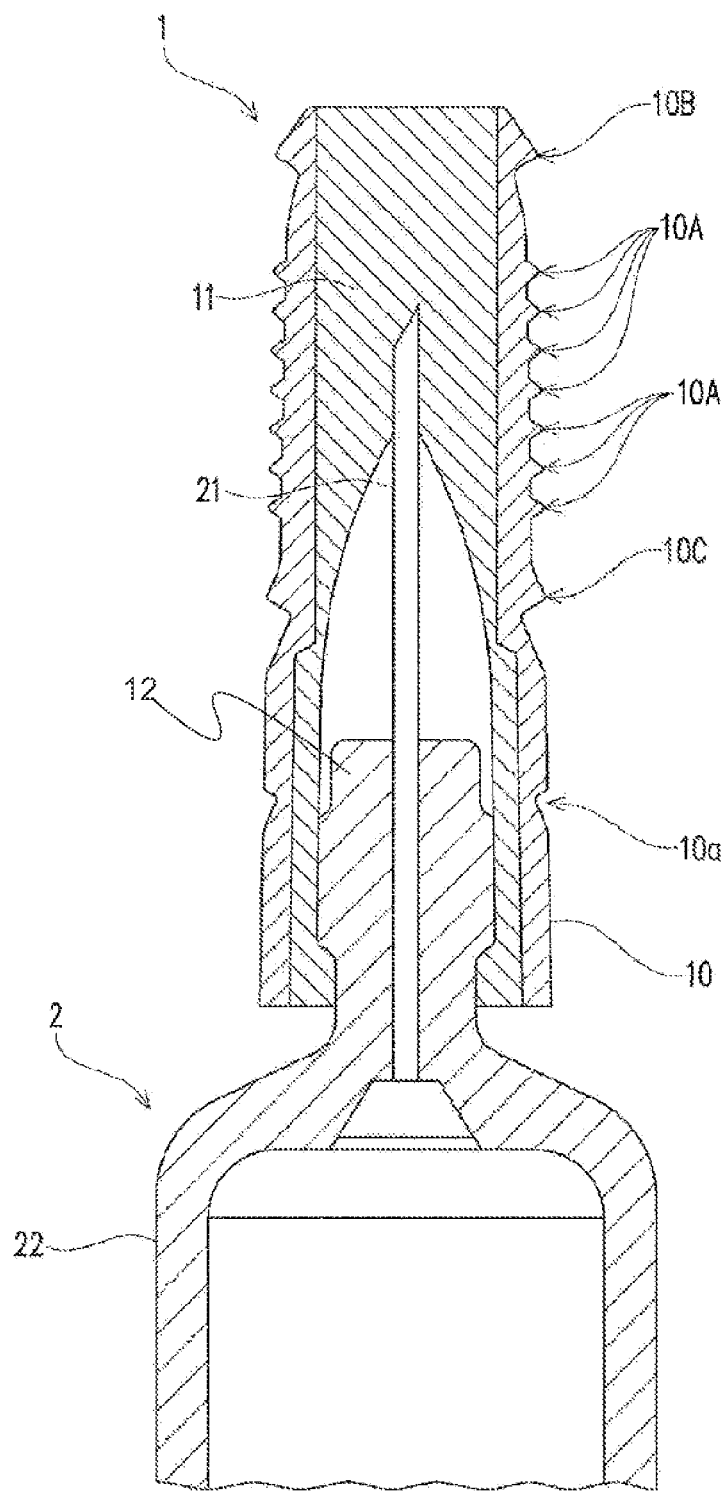
FIG. 1 is a sectional view showing a syringe cap according to an embodiment of the present invention when it is attached to a syringe body.

A syringe cap according to the present invention includes: a cylindrical cap body into which a needle is inserted from the proximal end toward the distal end and which is detachably attached to a syringe body to which the needle is attached; and at least one projection projecting from the outer circumferential surface of the cap body and extending in the circumferential direction of the cap body, wherein the projection includes: an apex located radially outward of the cap body from the outer circumferential surface of the cap body; a first inclined surface having a starting end located at the apex and having a terminal end located at a position on the side closer to the proximal end of the cap body than the starting end is, on the outer circumferential surface of the cap body; and a second inclined surface having a starting end located at the apex and having a terminal end located at a position on the side closer to the distal end of the cap body than the starting end is, on the outer circumferential surface of the cap body, and the shortest distance from the starting end to the terminal end of the first inclined surface is smaller than the shortest distance from the starting end to the terminal end of the second inclined surface.

According to the syringe cap configured as above, the first inclined surface of the projection is erected from the outer circumferential surface of the cap body. Therefore, when the cap body is pulled in a direction away from the syringe body, the user's hand abuts the first inclined surface of the projection and is caught thereby. This suppresses slip in detachment from the syringe body. As a result, the tension to the cap body is transmitted to the entire syringe cap, and therefore the syringe cap is easily detached. In particular, for a syringe with a small volume of 0.5 mL to 5.0 mL, preferably 1 mL, this effect is significant.

According to one aspect of the present invention, the configuration can be such that the cap body includes a tapered portion having an outer diameter that continuously decreases from the proximal end side toward the distal end side, and the projection is arranged in the tapered portion. As a result, and necessarily, the distal end side region of the cap body is more steeply inclined than the central region of the cap body. According to such a configuration, the cap body is tapered toward the distal end side, which facilitates the approach to the user's hand.

In this case, the configuration can be such that the inclination angle of the first inclined surface with respect to the axis of the cap body is the same as the inclination angle of the second inclined surface with respect to the axis of the cap body. According to such a configuration, the first inclined surface and the second inclined surface of the projection are likely to abut the user's hand uniformly, and therefore uncomfortable feeling to the user's hand is reduced. It is preferable that the inclination angle of the first inclined surface with respect to the axis of the cap body be 35 degrees or more and less than 90 degrees.

According to another aspect of the present invention, it is preferable that the projection be provided along the entire circumference of the cap body. According to such a configuration, the user's hand is reliably caught by the projections, even if any point in the circumferential direction of the cap body is pinched, so that slip in detachment from the syringe body is suppressed.

According to another aspect of the present invention, it is preferable to include a plurality of projections as set forth. It is preferable that the number of projections be 4 or more. The upper limit of the number of projections differs depending on the cap size and is not specifically limited, but is, for example, 20 or less, preferably 15 or less. In particular, for a syringe cap with a volume of 1 mL, the number of projections is preferably 3 to 15, further preferably 3 to 12. According to such a configuration, the slip in detachment from the syringe body is further suppressed by increasing the portions to catch the user's hand.

In this case, it is preferable that the plurality of projections be arranged at least in the central region in a direction in which the axis of the cap body extends, on the outer circumferential surface of the cap body. According to such a configuration, slip in detachment from the syringe body is suppressed in the central region of the cap body that generally has a high possibility of being pinched by the user.

In this case, it is preferable that at least one of the plurality of projections be higher than the other projections. According to such a configuration, the user's hand is easily caught by the high projection, and therefore the user's hand is caught by the high projection, even if the user's hand is not caught by the other projections, so that the syringe cap is easily detached.

In this case, the configuration can be such that all of the plurality of projections arranged in the central region have the same height. According to such a configuration, the user's hand uniformly abuts the plurality of projections, and thus uncomfortable feeling to the user's hand is reduced.

In this case, the configuration can be such that the plurality of projections include a projection that is arranged in at least one of a region on the distal end side from the central region and a region on the proximal end side from the central region, on the outer circumferential surface of the cap body, and that is higher than the projections arranged in the central region. According to such a configuration, the user's hand is easily caught by the high projection, and therefore the slip is suppressed more in the at least one of the region on the distal end side and the region on the proximal end side than in the central region.

In this case, it is preferable that the plurality of projections include projections that are arranged respectively in the region on the distal end side and the region on the proximal end side and that are higher than the plurality of projections arranged in the central region. According to such a configuration, the user's hand is easily caught by the projections that are high, and therefore slip is suppressed more in the region on the distal end side and the region on the proximal end side than in the central region.

In this case, it is preferable that the projection arranged in the region on the distal end side be higher than the projection arranged in the region on the proximal end side. According to such a configuration, the user's hand is easily caught by the high projection, and therefore the user's hand is caught by the high projection arranged in the region on the distal end side, even if the user's hand is not caught by the projection in the region on the proximal end side, so that the syringe cap is easily detached. Further, in the case where the user's hand is caught in the region on the distal end side in which the high projection is arranged, the distance between the user's hand and the syringe body is larger than in the case where the user's hand is caught in the central region or the region on the proximal end side of the cap body, and therefore the possibility that the needle contacts or pricks the user's hand when the syringe cap is detached is reduced.

In this case, it is preferable that the projection arranged in the region on the distal end side be highest in the plurality of projections. According to such a configuration, the user's hand is most easily caught by the highest projection, and therefore the user's hand is caught by the highest projection, even if the user's hand is not caught by the other projections, so that the syringe cap is easily detached. Further, in the case where the user's hand is caught in the region on the distal end side in which the highest projection is arranged, the distance between the user's hand and the syringe body is larger than in the case where the user's hand is caught in the central region or the region on the proximal end side of the cap body, and therefore the possibility that the needle contacts or pricks the user's hand when the syringe cap is detached is reduced.

A syringe with a needle according to the present invention includes: a syringe body that is internally fillable with drug; a needle attached to the distal end of the syringe body; and a syringe cap detachably attached to the syringe body and configured to cover the needle, wherein the syringe cap is the syringe cap according to any one of the aforementioned aspects. Such a configuration can exert the same actions and effects as the aforementioned syringe cap by including the syringe cap according to any one of the aforementioned aspects.

A prefilled syringe formulation of the present invention includes: a syringe body internally filled with drug; a needle attached to the distal end of the syringe body; and a syringe cap detachably attached to the syringe body and configured to cover the needle, wherein the syringe cap is any one of the aforementioned syringe caps. Such a configuration can exert the same actions and effects as the aforementioned syringe cap by including the syringe cap according to any one of the aforementioned aspects.

In this case, it is preferable that the aforementioned prefilled syringe formulation be a self-injectable formulation. According to such a configuration, it is easy to detach the syringe cap from the syringe body, even in the case where users of the prefilled syringe formulation are patients themselves, particularly, for hand-disabled persons such as arthritis patients.

As described above, the syringe cap of the present invention can exert an excellent effect of suppressing slip in detachment from the syringe body.

The syringe with a needle of the present invention can exert an excellent effect that the syringe cap is easily detached from the syringe body since it includes the aforementioned syringe cap.

The prefilled syringe formulation of the present invention can exert an excellent effect that the syringe cap is easily detached from the syringe body since it includes the aforementioned syringe cap.

Hereinafter, a syringe cap according to an embodiment of the present invention will be described with reference to FIG. 1 to FIG. 6.

As shown in FIG. 1, a prefilled syringe has a cylindrical syringe body 22 internally filled with drug, a needle 21 attached to the distal end of the syringe body 22, and a plunger (not shown) that is inserted into the syringe body 22 and is slidable in the axial direction of the syringe body 22. The prefilled syringe 2 is configured so that, when the plunger is pressed, the plunger slides to move toward the distal end of the syringe body 22 within the syringe body 22, and the drug filled in the syringe body 22 is extruded from the distal end of the needle 21.

The prefilled syringe 2 further includes a syringe cap 1 detachably attached to the syringe body 22 and configured to cover the needle 21.

Figure 2:
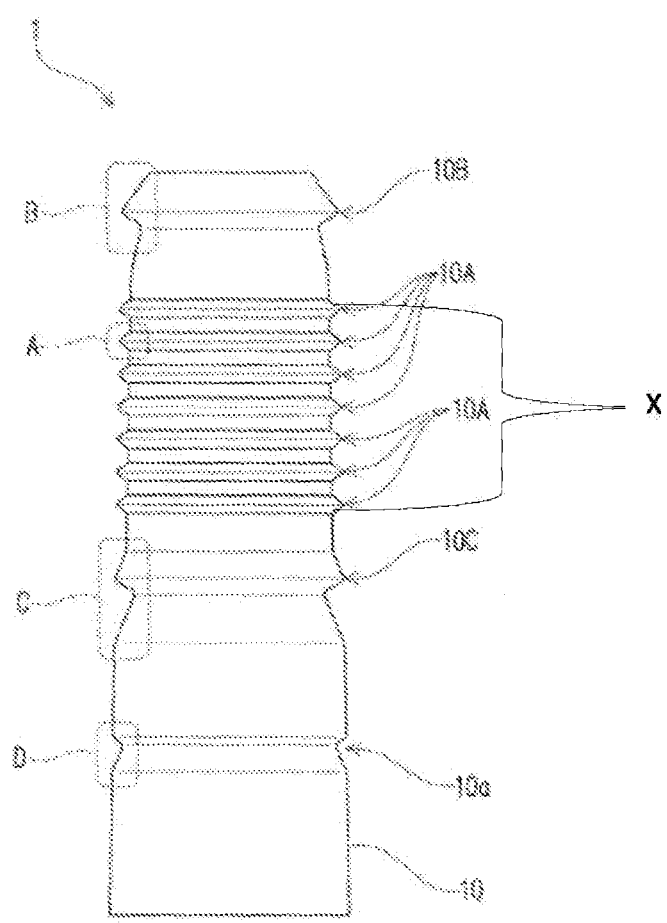
FIG. 2 is an overview of the syringe cap according to the aforementioned embodiment.

As shown in FIG. 1 and FIG. 2, the syringe cap 1 according to this embodiment includes a cap body 10 and a seal member 11.

The cap body 10 is formed into a cylindrical shape so that the needle 21 can be inserted thereinto from the proximal end toward the distal end.

Here, the cap body 10 will be specifically described. The cap body 10 has a cylindrical shape that is open at both ends. One of the openings on one end (proximal end) side of the cap body 10 serves as the insertion opening for the needle 21. In this embodiment, the needle 21 is inserted from the opening on the proximal end side of the cap body 10 toward the opening on the other end (distal end) side thereof.

The syringe cap 1 of this embodiment has at least one projection 10A, 10B, or 10C projecting from the outer circumferential surface of the cap body 10 and extending in the circumferential direction of the cap body 10. The projection 10A, 10B, or 10C of this embodiment is provided along the entire circumference of the cap body 10.

In this embodiment, the cap body 10 has a tapered portion having an outer diameter that continuously decreases from the proximal end side toward the distal end side, and the projection 10A is arranged in the tapered portion.

The syringe cap 1 of this embodiment includes a plurality of projections 10A, 10B, and 10C. The plurality of projections 10A, 10B, and 10C are arranged at least in the central region in the direction in which the axis of the cap body 10 extends, on the outer circumferential surface of the cap body 10. In this embodiment, a plurality (herein seven) of projections (hereinafter, referred to as first projections) 10A are arranged in the central region X, one projection (hereinafter, referred to as second projection) 10B is arranged in a region on the distal end side from the central region, and one projection (hereinafter, referred to as third projection) 10C is arranged in a region on the proximal end side from the central region. In the following description, the first projections 10A, the second projection 10B, the third projection 10C may be collectively referred to simply as projections. The number of projections is preferably 4 or more. The upper limit of the number of projections differs depending on the cap size and is not specifically limited, but is, for example, 20 or less, preferably 15 or less. In particular, for a syringe cap with a volume of 1 mL, the number of projections is preferably 3 to 15, further preferably 3 to 12.

Figure 3:
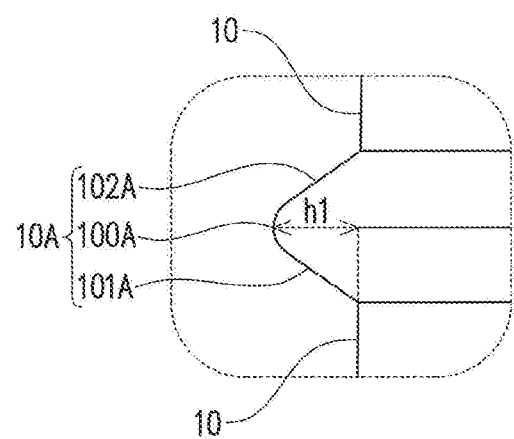
FIG. 3 is an enlarged view of A part in FIG. 2.

As shown in FIG. 3, each of the first projections 10A has an apex 100A, a first inclined surface 101A, and a second inclined surface 102A. The apex 100A is located radially outward of the cap body 10 from the outer circumferential surface of the cap body 10. The first inclined surface 101A has a starting end located at the apex 100A and has a terminal end located at a position on the side closer to the proximal end of the cap body 10 than the starting end is, on the outer circumferential surface of the cap body 10. The second inclined surface 102A has a starting end located at the apex 100A and has a terminal end located at a position on the side closer to the distal end of the cap body 10 than the starting end is, on the outer circumferential surface of the cap body 10. The shortest distance from the starting end to the terminal end of the first inclined surface 101A is smaller than the shortest distance from the starting end to the terminal end of the second inclined surface 102A.

In this embodiment, the inclination angle of the first inclined surface 101A of the first projection 10A with respect to the axis of the cap body 10 is the same as the inclination angle of the second inclined surface 102A of the first projection 10A with respect to the axis of the cap body 10. Further, all of the plurality of first projections 10A that are arranged in the central region have the same height h1. Further, the plurality of first projections 10A are arranged at equal intervals.

Figure 4:
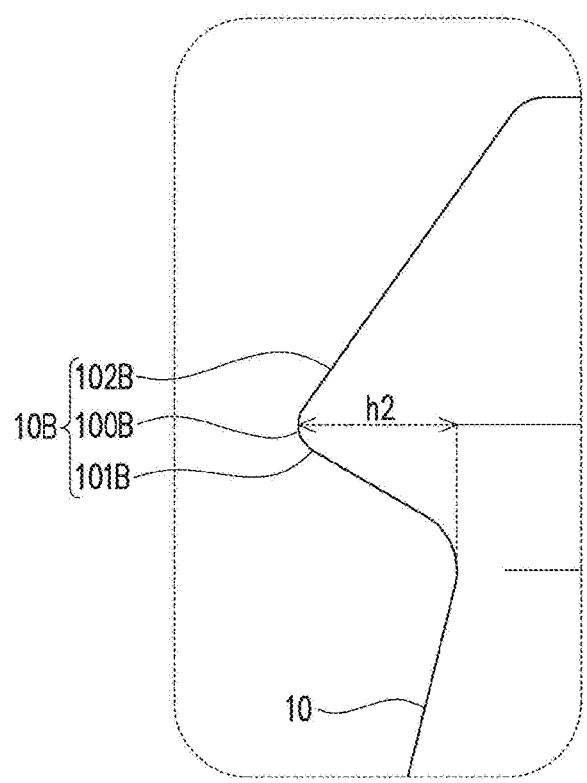
FIG. 4 is an enlarged view of B part in FIG. 2.

As shown in FIG. 4, the second projection 10B has an apex 100B, a first inclined surface 101B, and a second inclined surface 102B. The apex 100B is located radially outward of the cap body 10 from the outer circumferential surface of the cap body 10. The first inclined surface 101B has a starting end located at the apex 100B and has a terminal end located at a position on the side closer to the proximal end of the cap body 10 than the starting end is, on the outer circumferential surface of the cap body 10. The second inclined surface 102B has a starting end located at the apex 100B and has a terminal end located at a position on the side closer to the distal end of the cap body 10 than the starting end is, on the outer circumferential surface of the cap body 10. The shortest distance from the starting end to the terminal end of the first inclined surface 101B is smaller than the shortest distance from the starting end to the terminal end of the second inclined surface 102B.

Figure 5:
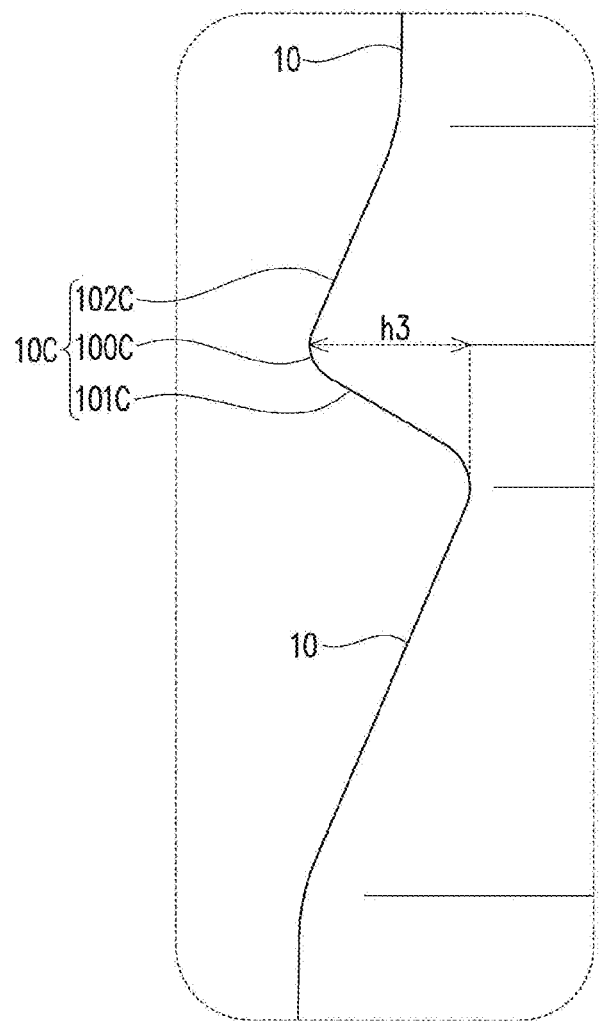
FIG. 5 is an enlarged view of C part in FIG. 2.

As shown in FIG. 5, the third projection 10C has an apex 100C, a first inclined surface 101C, and a second inclined surface 102C. The apex 100C is located radially outward of the cap body 10 from the outer circumferential surface of the cap body 10. The first inclined surface 101C has a starting end located at the apex 100C and has a terminal end located at a position on the side closer to the proximal end of the cap body 10 than the starting end is, on the outer circumferential surface of the cap body 10. The second inclined surface 102C has a starting end located at the apex 100C and has a terminal end located at a position on the side closer to the distal end of the cap body 10 than the starting end is, on the outer circumferential surface of the cap body 10. The shortest distance from the starting end to the terminal end of the first inclined surface 101C is smaller than the shortest distance from the starting end to the terminal end of the second inclined surface 102C. In this embodiment, the inclination of the outer circumferential surface of the cap body 10 located on the distal end side of the third projection 10C in the axial direction of the cap body 10 is smaller than the inclination of the outer circumferential surface of the cap body 10 located on the proximal end side of the third projection 10C in the axial direction of the cap body 10.

The inclination angles of the first inclined surfaces 101A, 101B, and 101C of the projections 10A, 10B, and 10C with respect to the axis of the cap body 10 are preferably 35 degrees or more and less than 90 degrees.

In the plurality of projections 10A, 10B, and 10C, at least one of heights h2 and h3 of the second projection 10B and the third projection 10C is larger than the height h1 of the other first projections 10A. In this embodiment, the heights h2 and h3 of both of the second projection 10B and the third projection 10C are larger than the height h1 of the first projections 10A. In this description, the height h1 refers to the distance from the position corresponding to the terminal end of the first inclined surface 101A to the apex 100A on the center line extending perpendicularly to the axis of the cap body 10 and passing through the apex 100A of the first projection 10A. The height h2 refers to the distance from the position corresponding to the terminal end of the first inclined surface 101B to the apex 100B on the center line extending perpendicularly to the axis of the cap body 10 and passing through the apex 100B of the second projection 10B. The height h3 refers to the distance from the position corresponding to the terminal end of the first inclined surface 101C to the apex 100C on the center line extending perpendicularly to the axis of the cap body 10 and passing through the apex 100C of the third projection 10C.

The plurality of projections 10A, 10B, and 10C include the second projection 10B and the third projection 10C that are arranged in at least one of a region on the distal end side from the central region and a region on the proximal end side from the central region, on the outer circumferential surface of the cap body 10, and that are higher than the first projections 10A arranged in the central region. In this embodiment, as mentioned above, the heights h2 and h3 of the second projection 10B and the third projection 10C arranged respectively in the region on the distal end side and the region on the proximal end side are larger than the height h1 of the first projections 10A arranged in the central region. That is, in this embodiment, the plurality of projections 10A, 10B, and 10C include the second projection 10B and the third projection 10C that are arranged respectively in the region on the distal end side and the region on the proximal end side and that are higher than the plurality of first projections 10A arranged in the central region.

In this embodiment, the height h2 of the second projection 10B arranged in the region on the distal end side is larger than the height h3 of the third projection 10C arranged in the region on the proximal end side. That is, in this embodiment, the height h2 of the second projection 10B arranged in the region on the distal end side is largest in the plurality of projections 10A, 10B, and 10C.

The syringe cap 1 of this embodiment further has a recess 10a recessed inwardly from the outer circumferential surface of the cap body 10 and extending in the circumferential direction of the cap body 10. In this embodiment, the recess 10a is provided in a region on the proximal end side in the direction in which the axis of the cap body 10 extends, on the outer circumferential surface of the cap body 10. Further, the recess 10a of this embodiment is provided along the entire circumference of the cap body 10.

Figure 6:
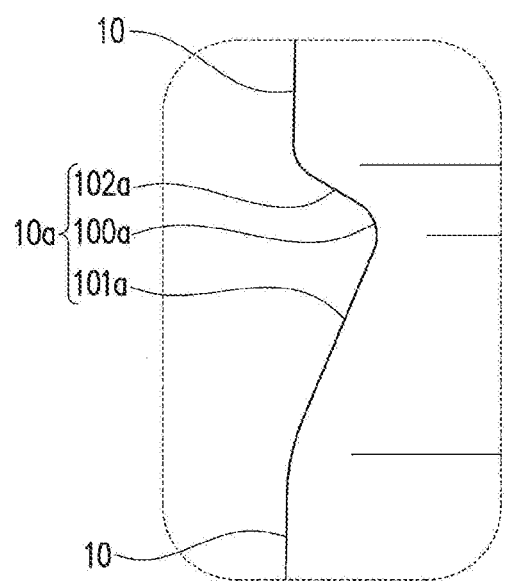
FIG. 6 is an enlarged view of D part in FIG. 2.

As shown in FIG. 6, the recess 10a has a bottom 100a, a first inclined surface 101a, and a second inclined surface 102a. The bottom 100a is located radially inward of the cap body 10 from the outer circumferential surface of the cap body 10. The first inclined surface 101a has a starting end located at the bottom 100a and has a terminal end located at a position on the side closer to the proximal end of the cap body 10 than the starting end is, on the outer circumferential surface of the cap body 10. The second inclined surface 102a has a starting end located at the bottom 100a and has a terminal end located at a position on the side closer to the distal end of the cap body 10 than the starting end is, on the outer circumferential surface of the cap body 10. The shortest distance from the starting end to the terminal end of the second inclined surface 102a is smaller than the shortest distance from the starting end to the terminal end of the first inclined surface 101a.

The seal member 11 is mounted inside the cap body 10. The seal member 11 is formed, for example, using an elastic material such as rubber. Further, the seal member 11 is formed to be fittable to the head 12 of the syringe body 22. The seal member 11 seals the head of the syringe body 22 in the state where the syringe cap 1 is attached to the syringe body 22. The seal member 11 is formed so that the needle 21 can be inserted thereinto.

The syringe cap 1 of this embodiment is processed, for example, by injection molding. Further, the syringe cap 1 of this embodiment is a resin molded product or a rubber molded product, for example. Examples of the resin include polypropylene and polyethylene.

The syringe cap 1 according to this embodiment includes: a cylindrical cap body 10 into which the needle 21 is inserted from the proximal end toward the distal end; and at least one first projection 10A, a second projection 10B, and a third projection 10C projecting from the outer circumferential surface of the cap body 10 and extending in the circumferential direction of the cap body 10, wherein the first projection 10A, the second projection 10B, and the third projection 10C respectively have: apices 100A, 100B, and 100C located radially outward of the cap body 10 from the outer circumferential surface of the cap body 10; first inclined surfaces 101A, 101B, and 101C that have starting ends respectively at the apices 100A, 100B, and 100C and have terminal ends on the outer circumferential surface of the cap body 10 located on the proximal end side of the cap body 10 from the starting ends; and second inclined surfaces 102A, 102B, and 102C have starting ends respectively at the apices 100A, 100B, and 100C and have terminal ends on the outer circumferential surface of the cap body 10 located on the distal end side of the cap body 10 from the starting ends, and the shortest distances from the starting ends to the terminal ends of the first inclined surfaces 101A, 101B, and 101C are smaller than the shortest distances from the starting ends to the terminal ends of the second inclined surfaces 102A, 102B, and 102C.

According to the syringe cap 1 configured as above, the first inclined surfaces 101A, 101B, and 101C of the first projection 10A, the second projection 10B, and the third projection 10C are erected from the outer circumferential surface of the cap body 10. Therefore, when the cap body 10 is pulled in a direction away from the syringe body 22, the user's hand abuts the first inclined surfaces 101A, 101B, and 101C of the first projection 10A, the second projection 10B and the third projection 10C, and is caught thereby. This suppresses slip in detachment from the syringe body 22. As a result, the tension to the cap body 10 is transmitted to the entire syringe cap 1, and therefore the syringe cap 1 is easily detached. In particular, for a syringe with a small volume of 0.5 mL to 5.0 mL, preferably 1 mL, this effect is significant.

In the syringe cap 1 according to this embodiment, the cap body 10 has a tapered portion having an outer diameter that continuously decreases from the proximal end side toward the distal end side, and the first projection 10A is arranged in the tapered portion. According to such a configuration, the cap body 10 is tapered toward the distal end side, which facilitates the approach to the user's hand.

In the syringe cap 1 according to this embodiment, the inclination angle of the first inclined surface 101A of the first projection 10A with respect to the axis of the cap body 10 is the same as the inclination angle of the second inclined surface 102A of the first projection 10A with respect to the axis of the cap body 10. According to such a configuration, the first inclined surface 101A and the second inclined surface 102A of the first projection 10A are likely to abut the user's hand uniformly, and therefore uncomfortable feeling to the user's hand is reduced.

In the syringe cap 1 according to this embodiment, the first projections 10A, the second projection 10B, and the third projection 10C are provided along the entire circumference of the cap body 10. According to such a configuration, the user's hand is reliably caught by the first projections 10A, the second projection 10B, and the third projection 10C, even if any point in the circumferential direction of the cap body 10 is pinched, so that slip in detachment from the syringe body 22 is suppressed.

The syringe cap 1 according to this embodiment has the plurality of projections 10A, 10B, and 10C. According to such a configuration, the slip in detachment from the syringe body 22 is further suppressed by increasing the portions to catch the user's hand.

In the syringe cap 1 according to this embodiment, the plurality of first projections 10A are arranged at least in the central region in the direction in which the axis of the cap body 10 extends, on the outer circumferential surface of the cap body 10. According to such a configuration, slip in detachment from the syringe body 22 is suppressed in the central region of the cap body 10 that generally has a high possibility of being pinched by the user.

In the syringe cap 1 according to this embodiment, the second projection 10B and the third projection 10C are higher than the other first projections 10A in the plurality of projections 10A, 10B, and 10C. According to such a configuration, the user's hand is easily caught by the high second projection 10B and the high third projection 10C, and therefore the user's hand is caught by the high second projection 10B and the high third projection 10C, even if the user's hand is not caught by the other first projections 10A, so that the syringe cap 1 is easily detached.

In the syringe cap 1 according to this embodiment, all of the plurality of first projections 10A arranged in the central region of the cap body 10 have the same height. According to such a configuration, the user's hand uniformly abuts the plurality of first projections 10A, and thus uncomfortable feeling to the user's hand is reduced.

In the syringe cap 1 according to this embodiment, the plurality of projections 10A, 10B, and 10C include the second projection 10B and the third projection 10C that are arranged respectively in the region on the distal end side and the region on the proximal end side and that are higher than the plurality of first projections 10A arranged in the central region. According to such a configuration, the user's hand is easily caught by the high second projection 10B and the high third projection 10C, and therefore slip is suppressed more in the region on the distal end side and the region on the proximal end side than in the central region.

In the syringe cap 1 according to this embodiment, the second projection 10B arranged in the region on the distal end side is highest in the plurality of projections 10A, 10B, and 10C. According to such a configuration, the user's hand is most easily caught by the highest second projection 10B, and therefore the user's hand is caught by the highest second projection 10B, even if the user's hand is not caught by the other first projections 10A and third projection 10C, so that the syringe cap 1 is easily detached. Further, in the case where the user's hand is caught in the region on the distal end side in which the highest second projection 10B is arranged, the distance between the user's hand and the syringe body 22 is larger than in the case where the user's hand is caught in the central region or the region on the proximal end side of the cap body 10, and therefore the possibility that the needle 21 contacts or pricks the user's hand when the syringe cap 1 is detached is reduced.

In the syringe cap 1 according to this embodiment, the second projection 10B arranged in the region on the distal end side is highest in the plurality of projections 10A, 10B, and 10C. According to such a configuration, the user's hand is most easily caught by the highest second projection 10B, and therefore the user's hand is caught by the highest second projection 10B, even if the user's hand is not caught by the other first projections 10A and third projection 10C, so that the syringe cap 1 is easily detached. Further, in the case where the user's hand is caught in the region on the distal end side in which the highest second projection 10B is arranged, the distance between the user's hand and the syringe body 21 is larger than in the case where the user's hand is caught in the central region or the region on the proximal end side of the cap body 10, and therefore the possibility that the needle 21 contacts or pricks the user's hand when the syringe cap 1 is detached is reduced.

The syringe cap of the present invention is not limited to the aforementioned embodiment, and it is a matter of course that various modifications can be made without departing from the gist of the present invention.

In the aforementioned embodiment, the cap body 10 having a cylindrical shape with both ends open has been described, but there is no limitation to this. The distal end side of the cap body 10 may be closed.

Figure 7:
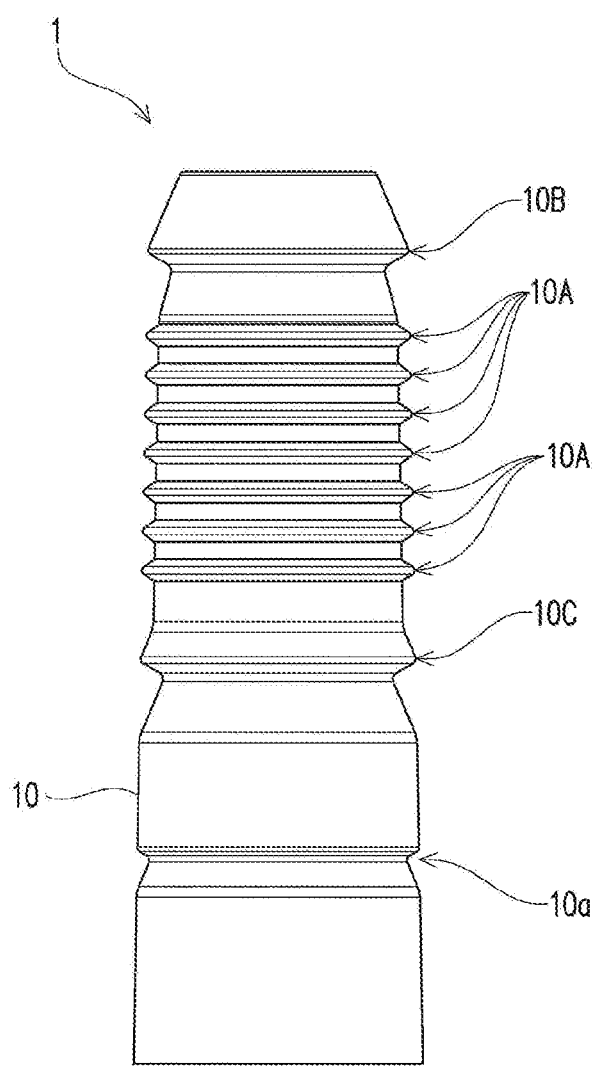
FIG. 7 is an overview of a syringe cap according to another embodiment of the present invention.
Figure 8:
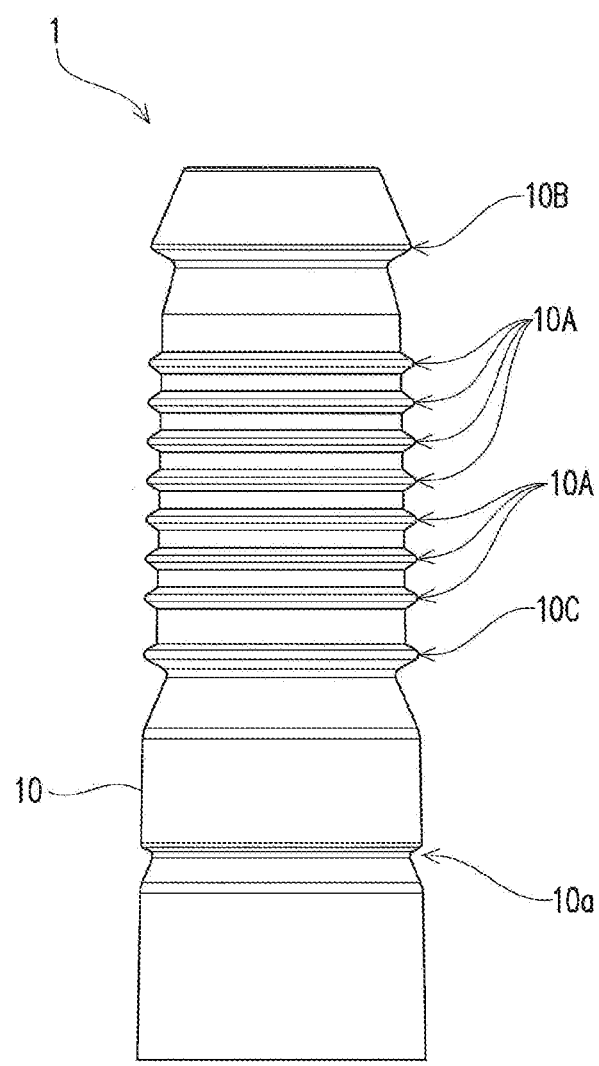
FIG. 8 is an overview of a syringe cap according to another embodiment of the present invention.
Figure 9:
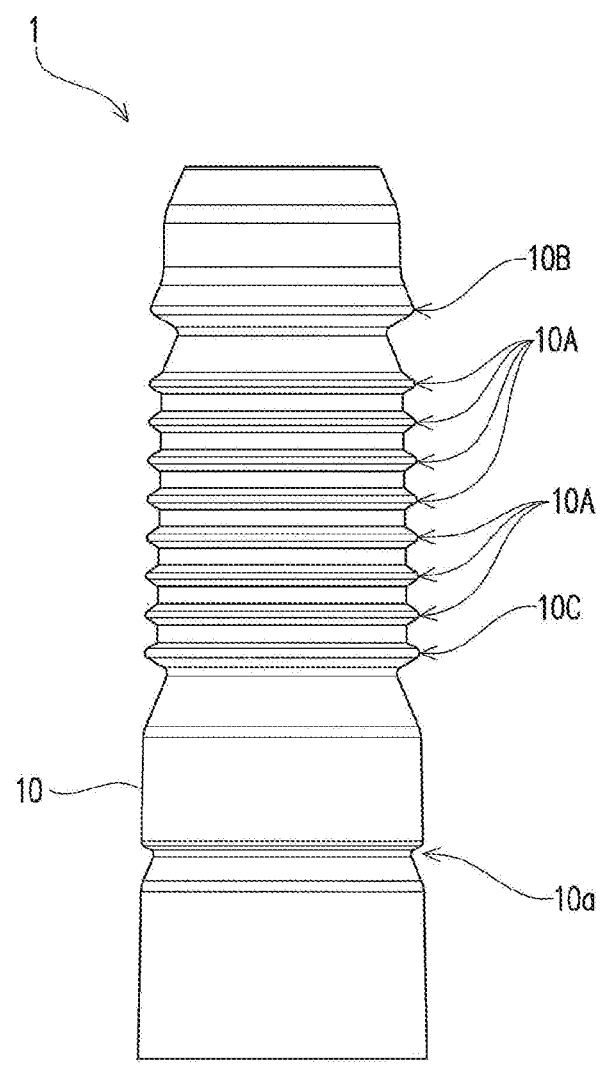
FIG. 9 is an overview of a syringe cap according to another embodiment of the present invention.

In the aforementioned embodiment, the positions and the heights h2 and h3 of the second projection 10B arranged in the region on the distal end side of the cap body 10 and the third projection 10C arranged in the region on the proximal end side of the cap body 10 can be appropriately changed, as shown in FIG. 7 to FIG. 9.

Figure 10:
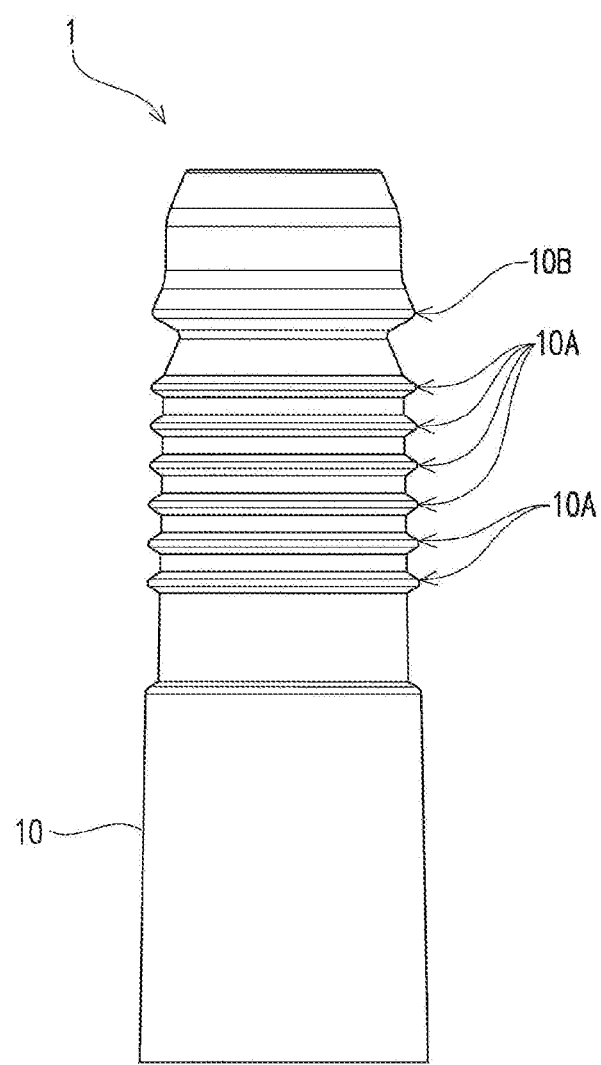
FIG. 10 is an overview of a syringe cap according to another embodiment of the present invention.

In the aforementioned embodiment, the second projection 10B and the third projection 10C that are higher than the first projections 10A arranged in the central region are provided respectively in the region on the distal end side and the region on the proximal end side, but there is no limitation to this. A projection that is higher than the first projections 10A arranged in the central region may be provided in one of the region on the distal end side and the region on the proximal end side. For example, as shown in FIG. 10, a syringe cap may have a plurality of first projections 10A arranged in the central region and the second projection 10B arranged in the region on the distal end side.

In the aforementioned embodiment, the single second projection 10B and the single third projection 10C are provided respectively in the region on the distal end side and the region on the proximal end side, but there is no limitation to this. For example, two or more second projections 10B may be provided in the region on the distal end side, and two or more third projections 10C may be provided in the region on the proximal end side.

In the aforementioned embodiment, a part of the cap body 10 serves as the tapered portion, but there is no limitation to this. For example, the entire cap body 10 may be the tapered portion, or the cap body 10 may have no tapered portion.

In the aforementioned embodiment, the inclination angle of the first inclined surface 101A of each of the plurality of first projections 10A arranged in the central region with respect to the axis of the cap body 10 is the same as the inclination angle of the second inclined surface 102A thereof with respect to the axis of the cap body 10, but there is no limitation to this. The inclination angle can be appropriately changed as long as the shortest distance from the starting end to the terminal end of the first inclined surface 101A is smaller than the shortest distance from the starting end to the terminal end of the second inclined surface 102A.

In the aforementioned embodiment, the case where the height h2 of the second projection 10B arranged in the region on the distal end side is higher than the height h3 of the third projection 10C arranged in the region on the proximal end side has been described, but there is no limitation to this. The height h2 of the second projection 10B on the distal end side may be the same as or lower than the height h3 of the third projection 10C on the proximal end side.

In the aforementioned embodiment, all of the plurality of first projections 10A arranged in the central region of the cap body 10 have the same height h1, but there is no limitation to this. For example, the plurality of first projections 10A arranged in the central region may have different heights from each other.

Figure 11:
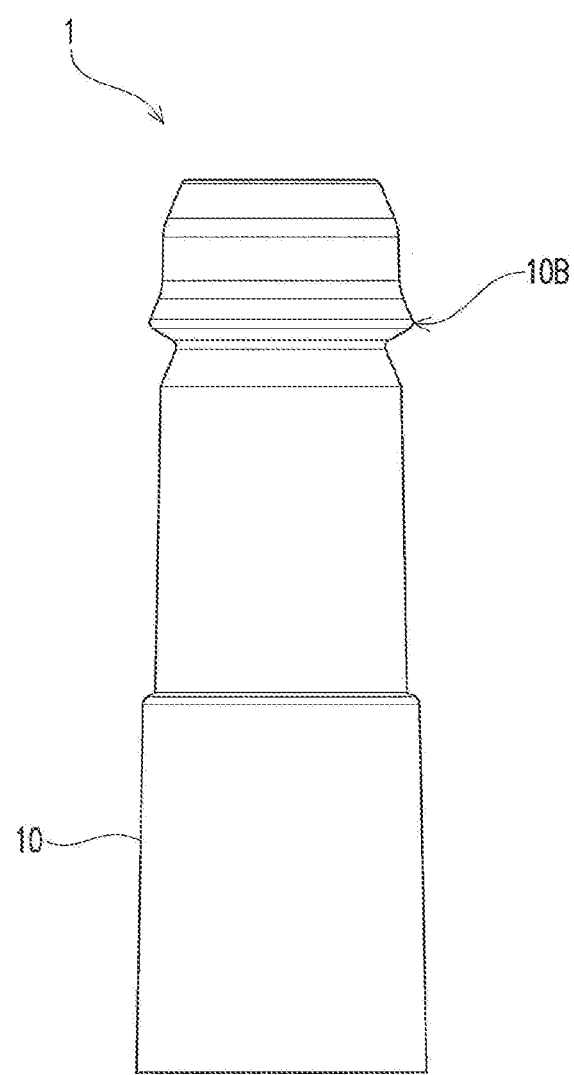
FIG. 11 is an overview of a syringe cap according to another embodiment of the present invention.
Figure 12:
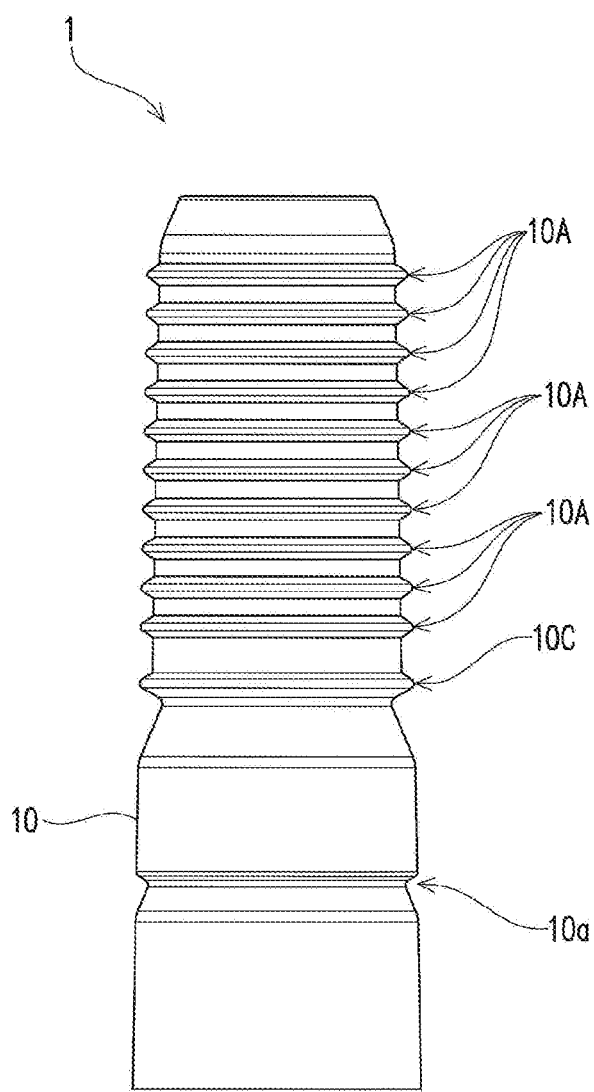
FIG. 12 is an overview of a syringe cap according to another embodiment of the present invention.
Figure 13:
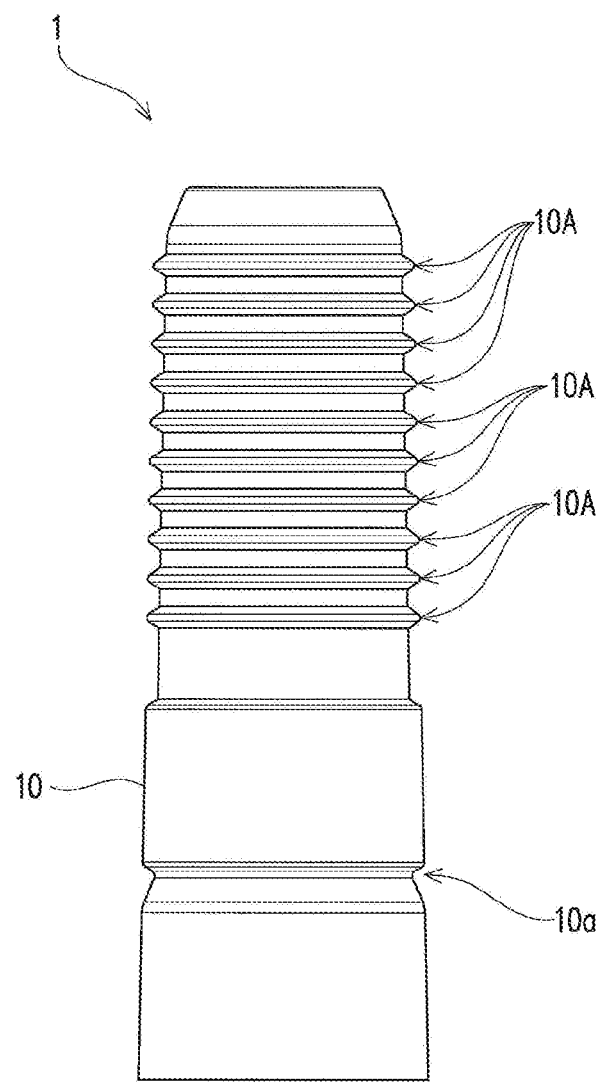
FIG. 13 is an overview of a syringe cap according to another embodiment of the present invention.
Figure 14:
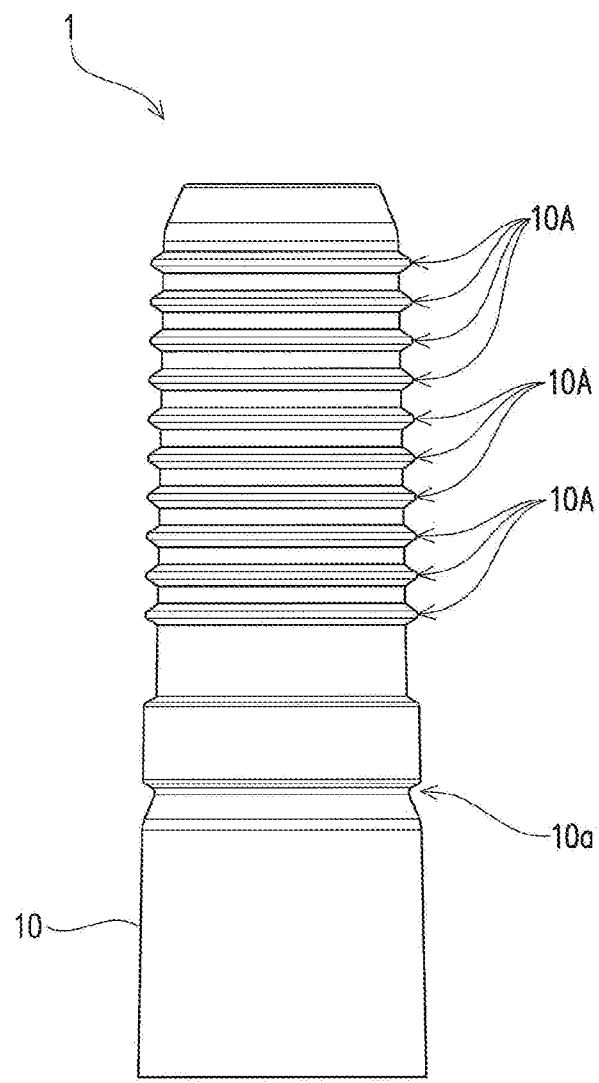
FIG. 14 is an overview of a syringe cap according to another embodiment of the present invention.
Figure 15:
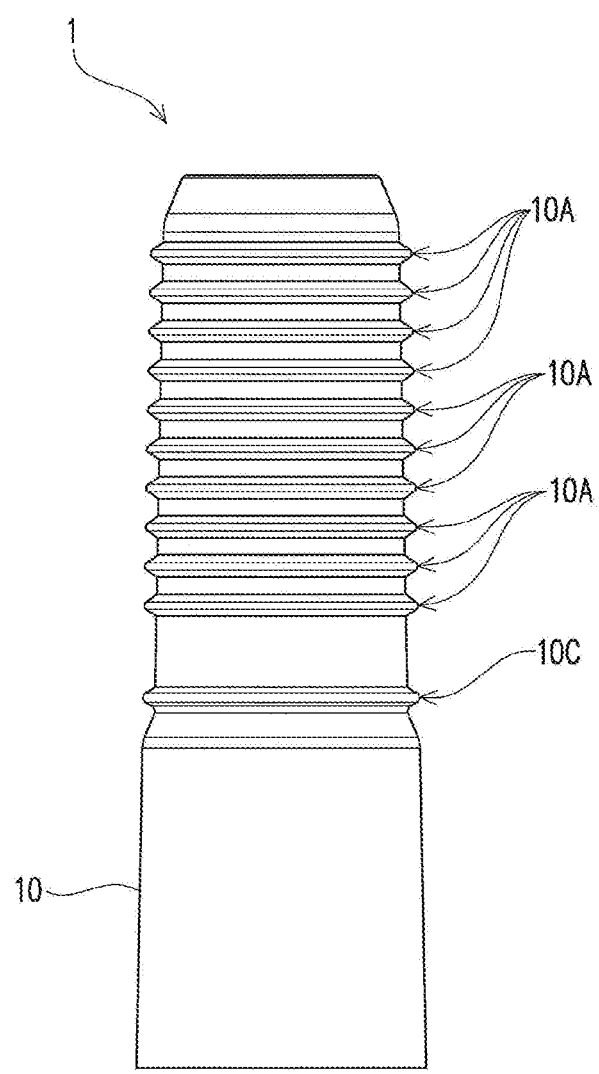
FIG. 15 is an overview of a syringe cap according to another embodiment of the present invention.
Figure 16:
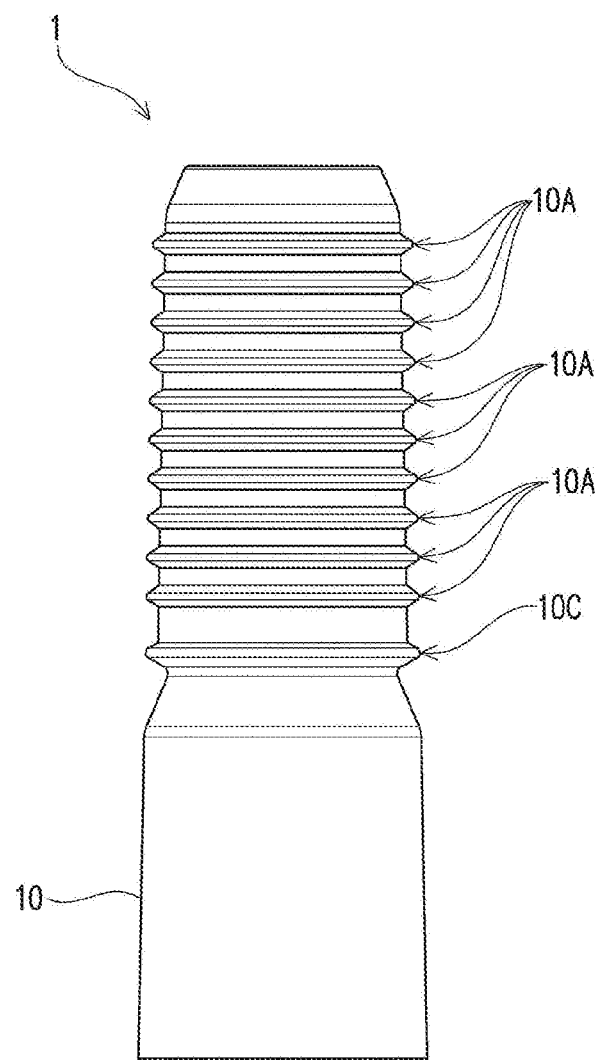
FIG. 16 is an overview of a syringe cap according to another embodiment of the present invention.
Figure 17:
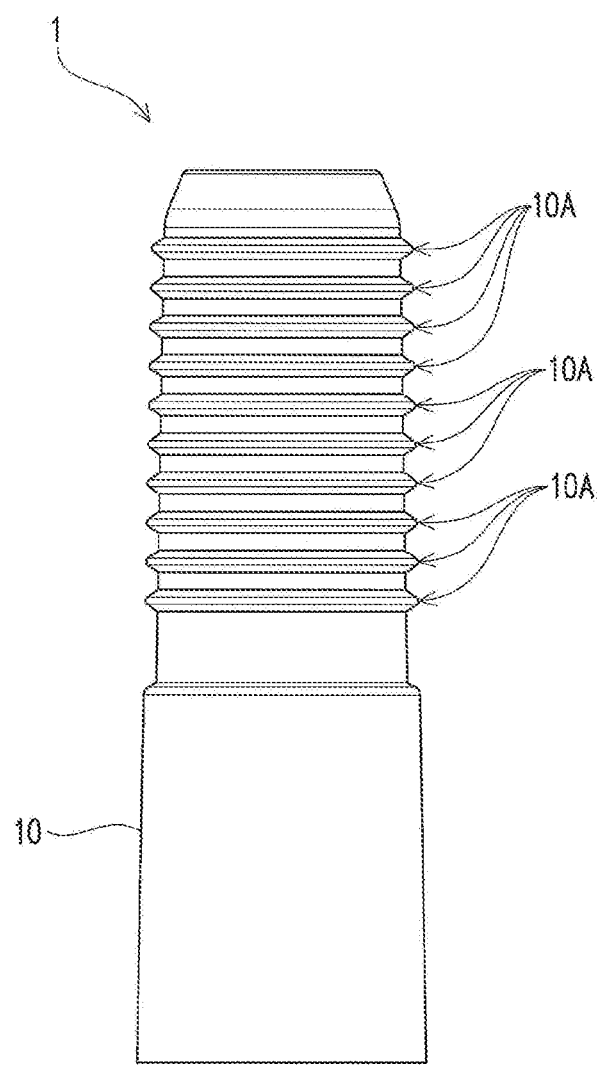
FIG. 17 is an overview of a syringe cap according to another embodiment of the present invention.

In the aforementioned embodiment, the syringe cap provided with the plurality of projections 10A, 10B, and 10C has been described, but there is no limitation to this, and the number of projections may be one. For example, as shown in FIG. 11, the syringe cap 1 may be provided with the single second projection 10B in the region on the distal end side. In FIG. 11, the second projection 10B is arranged on the region on the distal end of the cap body 10, but the position of the second projection 10B may be in the central region or the region on the proximal end side. Further, the height of the second projection 10B also can be appropriately changed.

In the aforementioned embodiment, the plurality of first projections 10A having the same height are provided only in the central region of the cap body 10, but there is no limitation to this, and the plurality of first projections 10A having the same the height can be provided in any region including the region on the distal end side, the central region, and the region on the proximal end side.

For example, as shown in FIG. 12 to FIG. 17, the syringe cap 1 may be configured so that the plurality of first projections 10A having the same height are arranged in the region on the distal end side and the central region. In the syringe cap 1 shown in FIG. 12, FIG. 15, and FIG. 16, the third projection 10C that is higher than the plurality of first projections 10A arranged in the region on the distal end side and the central region is arranged in the region on the proximal end side. In the syringe cap 1 shown in FIG. 13 and FIG. 14, the recess 10a is arranged in the region on the proximal end side.

Figure 18:
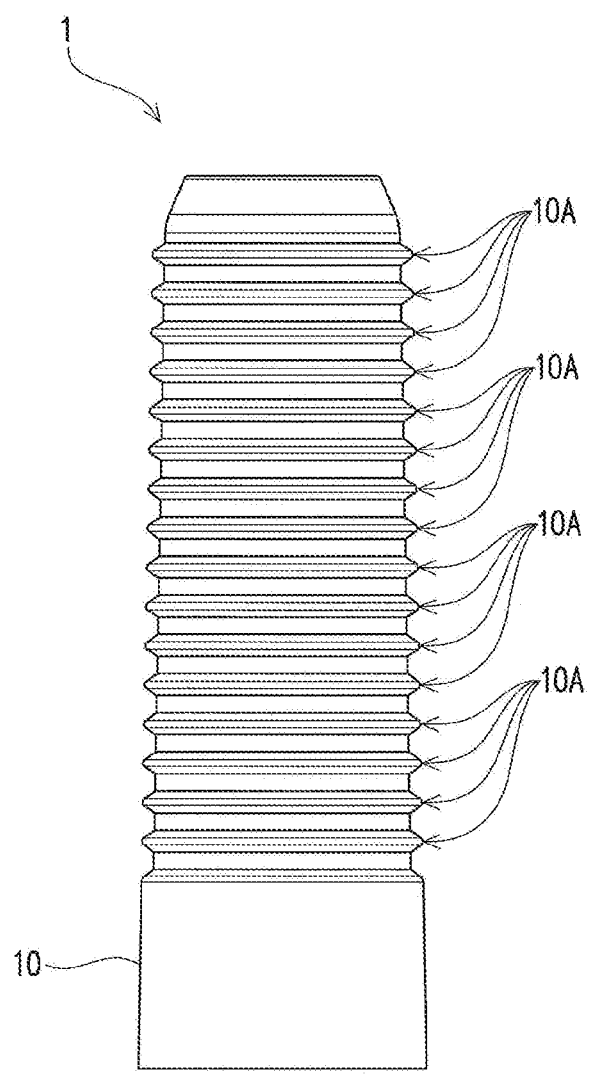
FIG. 18 is an overview of a syringe cap according to another embodiment of the present invention.

Further, as shown in FIG. 18, the syringe cap 1 may be configured so that the plurality of first projections 10A having the same height are provided in a region extending from the distal end side to the proximal end side.

Figure 19:
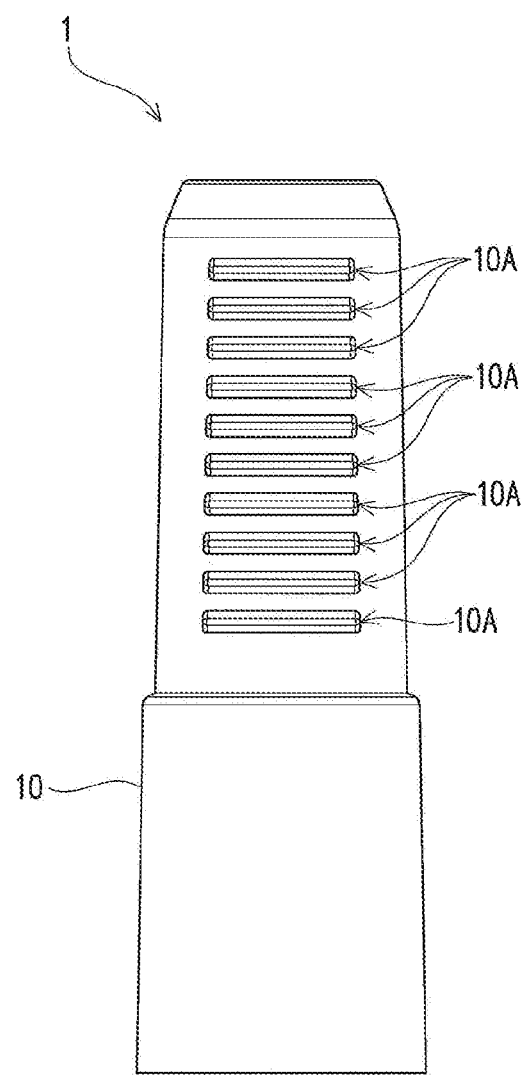
FIG. 19 is an overview of a syringe cap according to another embodiment of the present invention.

In the aforementioned embodiment, the first projection 10A, the second projection 10B, and the third projection 10C are provided along the entire circumference of the cap body 10, but there is no limitation to this. The first projection 10A, the second projection 10B, and the third projection 10C need only to be formed to extend in the circumferential direction of the cap body 10. For example, as shown in FIG. 19, the syringe cap 1 may be configured so that the plurality of first projections 10A having a specific length are arranged in the distal end region and the central region of the cap body 1.

In the aforementioned embodiment, the recess 10a is provided on the outer circumferential surface of the cap body 10, but there is no limitation to this, and the recess 10a may be omitted. Further, the position, depth, or the like of the recess 10a can be appropriately changed.

In the aforementioned embodiment, the recess 10a is provided along the entire circumference of the cap body 10, but there is no limitation to this, and the recess 10a having any length may be formed to extend in the circumferential direction of the cap body 10.

In the aforementioned embodiment, the seal member 11 is provided, but there is no limitation to this, and the seal member 11 may be omitted.

In the aforementioned embodiment, the prefilled syringe 2 in which the syringe body 22 filled with drug in advance is employed as a syringe (syringe with a needle) provided with the syringe cap 1, but there is no limitation to this, and a syringe with a needle in which the syringe body 22 is filled with drug afterward may be employed. Further, the syringe cap 1 may be attached to a syringe with a needle that has been separately prepared. As a syringe with a needle to which the syringe cap 1 of the aforementioned embodiment is attached, any syringe including a syringe body to which the syringe cap 1 is detachably attached and which can be internally filled with drug, and a needle attached to the distal end of the syringe body can be applied.

The prefilled syringe 2 including the syringe cap 1 of the aforementioned embodiment can be applied to prefilled syringe formulations. Examples of the prefilled syringe formulations include self-injectable formulations in which patients administer drugs by themselves.

REFERENCE SIGNS LIST

1: Syringe cap
10: Cap body
10A: First projection
10B: Second projection
10C: Third projection
100A, 100B, 100C: Apices of projections
101A, 101B, 101C: First inclined surfaces of projections
102A, 102B, 102C: Second inclined surfaces of projections
10a: Recess
100a: Bottom of recess
101a: First inclined surface of recess
102a: Second inclined surface of recess
11: Seal member
2: Prefilled Syringe
21: Needle
22: Syringe body

The invention claimed is:

1. A syringe cap comprising:
a cylindrical cap body into which a needle is inserted from a proximal end toward a distal end and is detachably attached to a syringe body to which the needle is attached; and
a plurality of projections projecting from an outer circumferential surface of the cylindrical cap body and extending around a circumference of the cylindrical cap body, wherein
the cylindrical cap body comprises:
a distal end side region formed on a distal end side of the cylindrical cap body; and
a central region located at a position between a proximal end side of the cylindrical cap body and the distal end side region,
wherein the distal end side region has a tapered shape with an outer diameter that decreases as being away from the central region in an extending direction of an axis of the cylindrical cap body
each of the plurality of projections comprises:
an apex located radially outward of the cylindrical cap body from the outer circumferential surface of the cylindrical cap body;
a first inclined surface having a starting end located at the apex and having a terminal end located at a position on a side closer to the proximal end side of the cylindrical cap body than the starting end is, on the outer circumferential surface of the cylindrical cap body; and
a second inclined surface having a starting end located at the apex and having a terminal end located at a position on a side closer to the distal end side of the cylindrical cap body than the starting end is, on the outer circumferential surface of the cylindrical cap body,
a shortest distance from the starting end to the terminal end of the first inclined surface is smaller than a shortest distance from the starting end to the terminal end of the second inclined surface, and
the plurality of projections comprise:
at least one projection arranged in the central region of the outer circumferential surface of the cylindrical cap body; and
one projection arranged at the distal end of the cylindrical cap body in the distal end side region, wherein
each of the plurality of projections has a height that is a distance from a position corresponding to the terminal end of the first inclined surface to the apex on a centerline extending perpendicularly to the axis of the cylindrical cap body passing through the apex, and
the height of the one projection arranged in the distal end side region is higher than the height of the at least one projection arranged in the central region
the plurality of projections further comprise one projection arranged in a proximal end side region from the central region, wherein a height of the one projection arranged in the proximal end side region from the central region is higher than a height of the at least one projection arranged in the central region.

2. The syringe cap according to claim 1, wherein the at least one projection arranged in the central region is configured to have an inclination angle of the first inclined surface with respect to the axis of the cylindrical cap body being the same as an inclination angle of the second inclined surface with respect to the axis of the cylindrical cap body.

3. The syringe cap according to claim 1, wherein each of the plurality of projections is provided along an entire circumference of the cylindrical cap body.

4. The syringe cap according to claim 1, wherein the at least one projection arranged in the central region comprises a plurality of projections having the same height.

5. A syringe with a needle, comprising:
a syringe body that is internally Tillable with a drug;
the needle attached to the syringe body; and
a syringe cap detachably attached to the syringe body and configured to cover the needle, wherein
the syringe cap is the syringe cap according to claim 1.

6. A prefilled syringe formulation comprising:
a syringe body internally filled with a drug;
a needle attached to the syringe body; and
a syringe cap detachably attached to the syringe body and configured to cover the needle, wherein
the syringe cap is the syringe cap according to claim 1.

7. The prefilled syringe formulation according to claim 6, being a self-injectable formulation.

8. The syringe cap according to claim 1, wherein the at least one projection of the central region comprises a plurality of projections, and
an interval in an axial direction between the projection of the plurality of the projections arranged in the central region closest to the distal end side of the cylindrical cap body and the one projection arranged at the distal end of the cylindrical cap body is larger than intervals in the axial direction between the plurality of projections in the central region.

9. The syringe cap according to claim 1, wherein the height of the one projection arranged on the distal end side region is larger than the height of the one projection arranged in the proximal end side region from the central region.

10. The syringe cap according to claim 1, further comprising a seal member that is mounted inside the cylindrical cap body to be in contact with the cylindrical cap body, the seal member is formed using an elastic material arranged to allow the needle to be insertable into the seal member in contact with the needle.

11. The syringe cap according to claim 10, wherein the seal member comprises a region in which the needle is inserted, and
the at least one projection arranged in the central region is arranged at a position corresponding to said seal member region in which the needle is inserted in an axial direction of the cylindrical cap body.

12. The syringe cap according to claim 11, wherein the at least one projection arranged in the central region comprises a plurality of projections,
one projection in the plurality of projections of the central region closest to the proximal end side is arranged in the proximal end side from the region of the seal member in which the needle is inserted, and
another projection in the plurality of projections of the central region closest to the distal end side is arranged in the distal end side from the region of the seal member in which the needle is inserted into.

* * * * *

UNITED STATES PATENT AND TRADEMARK OFFICE
CERTIFICATE OF CORRECTION

PATENT NO. : 11,839,749 B2
APPLICATION NO. : 15/315460
DATED : December 12, 2023
INVENTOR(S) : Rieko Shiozaki et al.

Page 1 of 1

It is certified that error appears in the above-identified patent and that said Letters Patent is hereby corrected as shown below:

In the Claims

Column 15, Line 20, Claim 5:
After "a syringe body that is internally", delete "Tillable" and insert --fillable--.

Signed and Sealed this
Twenty-seventh Day of August, 2024

Katherine Kelly Vidal
*Director of the United States Patent and Trademark Office*